United States Patent
Saito et al.

[11] Patent Number: 5,717,116
[45] Date of Patent: Feb. 10, 1998

[54] PROCESS FOR PRODUCING (R)-STYRENE OXIDES

[75] Inventors: Kenji Saito, Hirakata; Norio Kometani, Kishiwada; Azusa Fujiwara, Kawachinagano; Yukio Yoneyoshi, Otsu; Gohfu Suzukamo, Suita, all of Japan

[73] Assignee: Sumika Fine Chemicals Company, Limited, Osaka, Japan

[21] Appl. No.: 624,084

[22] Filed: Mar. 29, 1996

[30] Foreign Application Priority Data

Mar. 29, 1995 [JP] Japan .................................. 7-097715

[51] Int. Cl.$^6$ ...................... C07D 301/24; C07D 301/26
[52] U.S. Cl. ............................................ 549/522; 549/518
[58] Field of Search ........................... 549/522, 518

[56] References Cited

U.S. PATENT DOCUMENTS

5,266,485  11/1993  Sawa et al. ........................ 435/280

FOREIGN PATENT DOCUMENTS

7109231  4/1995  Japan.

OTHER PUBLICATIONS

Journal of Medicinal Chemistry, 1992, vol. 35, No. 16, pp. 3081–3084.

"Asymmetric Synthesis Using Chirally Modified Borohydrides. Part 3. Enantioselective Reduction of Ketones and Oxime Ethers with Reagents Prepared from Borane and Chiral Amino Alcohols", S. Itsuno et al., Journal Chem. Soc. Perkin Trans. 1985 pp. 2039–2044.

Niedizak, Margolin, Tetrahedron: Asymmetry, 2(2), 1991 pp. 113–122.

*Primary Examiner*—John M. Ford
*Attorney, Agent, or Firm*—Birch, Stewart, Kolasch & Birch, LLP

[57] ABSTRACT

The present invention provides a process for producing (R)-styrene oxides represented by the formula (1):

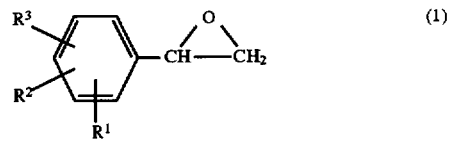

wherein $R^1$, $R^2$, $R^3$ and X are as defined in the specification, which comprises treating a mixture of (R)- and (S)-phenylhalogenomethylcarbinols with a lipase in the presence of a carboxylate to preferentially convert the (S)-phenylhalogenomethylcarbinols, and treating a mixture of the formed carbinol alkylates (3) and (R)-phenylhalogenomethylcarbinols with a base to cyclize the (R)-phenylhalogenomethylcarbinols, and also provides an industrially excellent process for producing (R)-styrene oxides (1) which comprises using a mixture enriched with (R)-phenylhalogenomethylcarbinols as the mixture of (R)- and (S)-phenylhalogenomethylcarbinols (2).

18 Claims, No Drawings

PROCESS FOR PRODUCING (R)-STYRENE OXIDES

FIELD OF THE INVENTION

The present invention relates to a process for producing (R)-styrene oxides. More particularly, it relates to a process for producing (R)-styrene oxides which comprises treating a mixture of (S)- and (R)-phenylhalogenomethylcarbinols with a specific enzyme in the presence of a carboxylate to selectively esterify the (S)-phenylhalogenomethylcarbinols, followed by treatment with a base.

BACKGROUND OF THE INVENTION (R)-Styrene oxides are compounds which are useful as a production intermediate for a remedy for diabetes, remedy for hyperglycemia, remedy or preventive for obesity, etc. As the production process thereof, e.g. process for producing (R)-m-chlorostyrene oxide, a conventional known process includes chlorinating m-chloroacetophenone to form chloromethyl m-chlorophenyl ketone, reacting this with a CBS catalyst to conduct asymmetric reduction to obtain a corresponding optically active chlorohydrin, and treating the optically active chlorohydrin with a base to conduct cyclization (J. Med. Chem., 35 3081 (1992)). Another process includes reacting bromomethyl m-chlorophenyl ketone with a microorganism to obtain optically active bromomethyl-m-chlorophenylcarbinol, and treating this with a base to conduct cyclization (Japanese Patent Kokai (Laid-Open) No. 4-218384), etc.

However, in the former process, the optical purity of the resulting (R)-m-chlorostyrene oxide is merely about 85% ee, and it is not satisfactory in view of the desired optical purity of the objective product. In the latter process, the resulting product is sufficient in optical purity, but large-scale equipment is required because a diluted solution (substrate concentration: about 0.5%) is required in the step employing the microorganism. Therefore, this process is not satisfactory because of the equipment requirements which reduce the efficiency of the plant facility.

The present inventors have studied intensively processes for producing (R)-styrene oxides so as to improve the drawbacks of these known processes. As a result, the inventors have discovered that, (S)-phenylhalogenomethylcarbinols are selectively esterified by treating a mixture of (R)- and (S)-phenylhalogenomethylcarbinols with a specific enzyme in the presence of a carboxylate, and then the unreacted (R)-phenylhalogenomethylcarbinols are selectively cyclized by treatment with a base, thereby producing the objective (R)-styrene oxides having high optical purity with improved efficiency. It has also been found that the objective (R)-styrene oxide can be produced, on an advantageously industrial scale, by using a mixture enriched with (R)-phenylhalogenomethylcarbinols as the mixture of (R)- and (S)-phenylhalogenomethylcarbinols. Thus, the present invention has been accomplished.

SUMMARY OF THE INVENTION

An object of the present invention is to provide a process for producing the objective (R)-styrene oxides having high optical purity with good efficiency.

This and other objects and advantages of the present invention will become apparent to those skilled in the art from the following description.

That is, the present invention provides an industrially excellent process for producing (R)-styrene oxides represented by the formula (1):

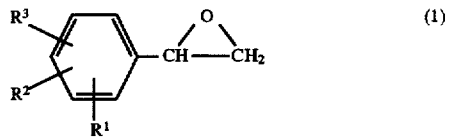

herein $R^1$ is a halogen atom, a lower alkyl group, a lower alkoxy group or a trifluoromethyl group; $R^2$ and $R^3$ independently indicate a hydrogen atom, a halogen atom, a lower alkyl group, a lower alkoxy group or a trifluoromethyl group, or $R^2$ and $R^3$ together form a methylenedioxy group, which comprises treating a mixture of (R)- and (S)-phenylhalogenomethylcarbinols represented by the formula (2):

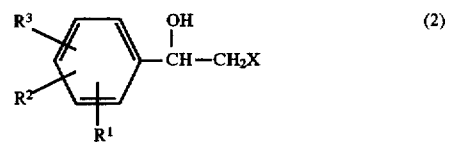

wherein $R^1$, $R^2$ and $R^3$ are as defined above, and X is a halogen atom, with a lipase in the presence of a carboxylate to preferentially convert the (S)-phenylhalogenomethylcarbinols (2) into carbinol alkylates represented by the formula (3):

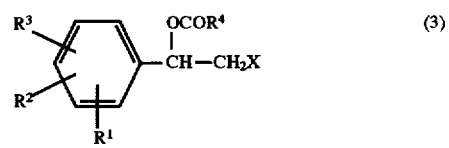

wherein $R^1$, $R^2$, $R^3$ and X are as defined above; and $R^4$ is a substituted or non-substituted lower alkyl group, and treating a mixture of the formed carbinol alkylates (3) and (R)-phenylhalogenomethylcarbinols (2) with a base to cyclize the (R)-phenylhalogenomethylcarbinols (2). Note that the structures in the formulas are plannar structures, not stereoscopic structures, and that the stereoisomeric characteristics are indicated by the use of "(R)-" for the (R)-isomer and "(S)-" for the (S)-isomer.

The present invention also provides an industrially excellent process for producing (R)-styrene oxides (1) which comprises using a mixture enriched with (R)-phenylhalogenomethylcarbinols as the mixture of (R)- and (S)-phenylhalogenomethylcarbinols (2).

DETAILED DESCRIPTION OF THE INVENTION

Hereinafter, the present invention will be explained in detail.

The present invention is characterized by treating a mixture of (R)- and (S)-phenylhalogenomethylcarbinols with a lipase to preferentially esterify the (S)-phenylhalogenomethylcarbinols and treating the resulting reaction mixture with a base to cyclize the unreacted (R)-phenylhalogenomethylcarbinols, and is explained below with regard to the step of treatment with a lipase and treatment to produce cyclization.

Lipase treatment

Examples of the substituent $R^1$ in the phenylhalogenomethylcarbinols (2) as the substrate of the lipase treatment include halogen atoms such as a fluorine atom, chlorine atom, bromine atom, etc.; lower alkyl groups such as a methyl group, ethyl group, propyl group, butyl group, pentyl group, etc.; lower alkoxy groups such as a methoxy group, ethoxy group, propoxy group, butoxy group, pentoxy group, etc.; trifluoromethyl group, etc.

Examples of the substituents $R^2$ and $R^3$ include a hydrogen atom, a halogen atom which is the same as that of $R^1$, lower alkyl group which is the same as that of $R^1$, lower alkoxy group which is the same as that of $R^1$, trifluoromethyl group, methylenedioxy group formed together by $R^2$ and $R^3$, etc. Examples of the substituent X include a chlorine atom, bromine atom, etc.

Specific examples of the phenylhalogenomethylcarbinols (2) wherein X is a bromine atom include bromomethyl-3'-chlorophenylcarbinol, bromomethyl-3'-bromophenylcarbinol, bromomethyl-3'-fluorophenylcarbinol, bromomethyl-3'-methylphenylcarbinol, bromomethyl-3'-methoxyphenylcarbinol, bromomethyl-3'-trifluoromethylphenylcarbinol, bromomethyl-4'-chlorophenylcarbinol, bromomethyl-4'-bromophenylcarbinol, bromomethyl-4'-fluorophenylcarbinol, bromomethyl-4'-methylphenylcarbinol, bromomethyl-4'-methoxyphenylcarbinol, bromomethyl-4'-trifluoromethylphenylcarbinol, bromomethyl-2'-chlorophenylcarbinol, bromomethyl-2'-bromophenylcarbinol, bromomethyl-2'-fluorophenylcarbinol, bromomethyl-2'-methylphenylcarbinol, bromomethyl-2'-methoxyphenylcarbinol, bromomethyl-2'-trifluoromethylphenylcarbinol, bromomethyl-3'-chloro-2'-methoxyphenylcarbinol, bromomethyl-3'-bromo-2'-methoxyphenylcarbinol, bromomethyl-3'-fluoro-2'-methoxyphenylcarbinol, bromomethyl-2'-methoxy-3'-methylphenylcarbinol, bromomethyl-2',3'-dimethoxyphenylcarbinol, bromomethyl-3'-methoxy-2'-trifluoromethylphenylcarbinol, bromomethyl-2',4'-dichlorophenylcarbinol, bromomethyl-4'-bromo-2'-chlorophenylcarbinol, bromomethyl-2'-chloro-4'-fluorophenylcarbinol, bromomethyl-2'-chloro-4'-methoxyphenylcarbinol, bromomethyl-2'-chloro-4'-methylphenylcarbinol, bromomethyl-2'-chloro-4'-trifluoromethylphenylcarbinol, bromomethyl-3'-chloro-5'-trifluoromethylphenylcarbinol, bromomethyl-3'-bromo-5'-trifluoromethylphenylcarbinol, bromomethyl-5'-fluoro-3'-trifluoromethylphenylcarbinol, bromomethyl-5'-methyl-3'-trifluoromethylphenylcarbinol, bromomethyl-5'-methoxy-3'-trifluoromethylphenylcarbinol, bromomethyl-3',5'-ditrifluoromethylphenylcarbinol, bromomethyl-3',5'-dichlorophenylcarbinol, bromomethyl-3',5'-dibromophenylcarbinol, bromomethyl-3',5'-difluorophenylcarbinol, bromomethyl-2',4',6'-trifluorphenylcarbinol, bromomethyl-2',4',6'-trichlorophenylcarbinol, bromomethyl-2',4',6'-tribromophenylcarbinol, bromomethyl-3',4'-methylenedioxyphenylcarbinol, etc. When X is a chlorine atom, examples thereof include the above compounds wherein bromomethyl is replaced by chloromethyl.

Among them, bromomethyl-3'-chlorophenylcarbinol, bromomethyl-3'-bromophenylcarbinol, bromomethyl-3'-fluorophenylcarbinol, bromomethyl-3'-methylphenylcarbinol, bromomethyl-3'-methoxyphenylcarbinol, bromomethyl-3'-trifluoromethylphenylcarbinol, chloromethyl-3'-chlorophenylcarbinol, chloromethyl-3'-bromophenylcarbinol, chloromethyl-3'-fluorophenylcarbinol, chloromethyl-3'-methylphenylcarbinol, chloromethyl-3'-methoxyphenylcarbinol and chloromethyl-3'-trifluoromethylphenylcarbinol are preferred, and bromomethyl-3'-chlorophenylcarbinol and chloromethyl-3'-chlorophenylcarbinols are more preferred.

Regarding the mixture of (R)- and (S)-phenylhalogenomethylcarbinols, the proportion of (R)- to (S)-phenylhalogenomethylcarbinols is not specifically limited and such mixtures enriched with the (R)-phenylhalogenomethylcarbinols are preferably used. For example, those mixtures containing not less than 70% of the (R)-phenylhalogenomethylcarbinols are preferred, and those mixtures containing not less than 80% of the (R)-phenylhalogenomethylcarbinols are more preferred.

The mixture enriched with the (R)-phenylhalogenomethylcarbinols (2) can be produced by subjecting the phenyl halogenomethyl ketones (4) to asymmetric reduction as described hereinafter.

The lipases used in the lipase treatment of the above phenylhalogenomethylcarbinols (2) act on the phenylhalogenomethylcarbinols (2) in the presence of a carboxylate to esterify them, but has a substrate specificity, that is, the reaction rate is extremely small for the (R)-phenylhalogenomethylcarbinols in comparison with the (S)-phenylhalogenomethylcarbinols.

Among them, a lipase produced by microorganism is preferred. Examples of the lipase include lipases produced by bacteria, lipases produced by Alcaligenes species, e.g. lipase QL and lipase PL (manufactured by Meito Sangyo Co., Ltd.); lipases produced by Achromobacter species, e.g. Lipase AL (manufactured by Meito Sangyo Co., Ltd.); lipase produced by Pseudomonas species, e.g. Lipase PS (manufactured by Amano Seiyaku Co., Ltd.); etc. Examples of the other lipases include lipase produced by Candida species, e.g. Lipase AY Amano 30 (manufactured by Amano Seiyaku Co., Ltd.), Lipase MY (manufactured by Meito Sangyo Co., Ltd.) and Lipase OF (manufactured by Meito Sangyo Co., Ltd); lipase produced by Aspergilus species, e.g. Lipase A Amano 6 (manufactured by Amano Seiyaku Co., Ltd.); lipase produced by Rhizopus species, e.g. Lipase F-AP15 (manufactured by Amano Seiyaku Co., Ltd.), Pneulase F (manufactured by Amano Seiyaku Co., Ltd.) and Lipase Saiken 100 (manufactured by Nagase Sangyo Co., Ltd.); lipases produced by Mucol species, e.g. Lipase F-AP15 (manufactured by Amano Seiyaku Co., Ltd.) and Lipase M Amano 10 (manufactured by Amano Seiyaku Co., Ltd.); etc.

Among lipase produced by microorganism, lipase produced by bacteria are preferred because the lipases produced by bacteria efficiently perform the esterification reaction. Lipases produced by Alcaligenes species, Achromobacter species and Pseudomonae species are preferred. Among them, Lipase QL produced by Alcaligenes species is particularly preferred.

The lipase is usually used in the amount of about 0.1 to 10% by weight to the (S)-phenylhalogenomethylcarbinols (2). Since the lipase can be recovered and used again, the reaction rate can be increased by using the lipase in the amount exceeding 10% by weight.

As the acyl group donor in the esterification reaction by lipase, a carboxylate is used. Examples of the carboxylate include vinyl esters, cyclohexyl esters and isopropenyl esters of carboxylic acids usually having 2 to 18 carbon atoms (e.g. acetic acid, chloroacetic acid, propionic acid, butyric acid, valeric acid, caproic acid, caprylic acid, lauric acid, palmitic acid, stearic acid, etc.). Among them, esters of acetic acid are preferred in view of the reaction rate of esterification.

The amount of the carboxylate is usually at least 2 moles per one mole of the (S)-phenylhalogenomethylcarbinols (2).

$R^4$ in the carbinol alkylates (3) depends on the carboxylate used. When ester of acetic acid is used as the carboxylate, $R^4$ is methyl group. When ester of caprylic acid is used, $R^4$ is heptyl group. Examples of $R^4$ are a methyl group, chloromethyl group, ethyl group, propyl group, butyl group, pentyl group, heptyl group, undecyl group, pentadecyl group, heptadecyl group.

The esterification reaction is conducted by mixing a reaction solvent, a mixture of (S)- and (R)-phenylhalogenomethylcarbinols (2) as the raw material, a lipase and a carboxylate as the acyl group donor with stirring. The reaction temperature is usually about 10° to 65° C., and it is preferred to suitably select an optimum temperature according to a temperature dependence of each lipase. In the case of the lipase produced by Alcaligenes species, e.g. Lipase QL (manufactured by Meito Sangyo Co., Ltd.) or Lipase PL (manufactured by Meito Sangyo Co., Ltd.), the reaction temperature is usually about 30° to 60° C., preferably about 35° to 55° C.

As the reaction solvent, for example, there can be used aromatic hydrocarbons such as benzene, toluene, etc.; aliphatic hydrocarbons such as pentane, hexane, cyclohexane, etc.; ethers such as dimethyl ether, methyl tert-butyl ether, etc.; ester solvents such as vinyl acetate, vinyl benzoate, etc. The solvent is usually used in such an amount that the concentration of the raw compound becomes about 3 to 50% by weight, preferably about 5 to 40% by weight.

The esterification reaction can be monitored by high performance chromatography with an optically active column (e.g. SUMICHIRAL OA-2500I made by Sumika Chemical Analysis Service Ltd., hexane/1,2-dichloroethane/ethanol=400:40:1) and the point where the amount of the (S)-phenylhalogenomethylcarbinols reached a value smaller than the detection limitation may be taken as the end point of the reaction.

Further, it is also preferred to react the lipase in the presence of a phenolic compound, thereby extremely increasing the reaction rate. Therefore, the amount of the lipase, carboxylate, etc. can also be reduced.

Examples of the phenolic compound include 2,6-di-tert-butyl-4-methylphenol (BHT), 2,6-di-tert-butylphenol, 2-tert-butyl-4-methylphenol, etc. The amount is usually about 0.1 to 5% by weight, based on the amount of the phenylhalogenomethylcarbinols (2).

After the reaction, for example, the lipase is removed from the reaction mixture by filtration to obtain a mixture of carbinol alkylates (3) and (R)-phenylhalogenomethylcarbinols (2). Such a mixture can be subjected to a cyclization treatment as the next step as it is, or after the solvent is distilled off.

Cyclization treatment

Examples of the base used for reacting with the mixture of carbinol alkylates (3) and (R)-phenylhalogenomethylcarbinols (2) to cyclize the (R)-phenylhalogenomethylcarbinols (2) include alkali metal hydroxides such as sodium hydroxide, potassium hydroxide, etc.; alkali metal carbonates such as sodium carbonate, potassium carbonate, etc.; alkali metal alkoxides such as sodium methoxide, potassium methoxide, potassium t-butoxide, etc.; organic bases such as triethylamine, etc. (Org. Synth., 1, 185 (1941), J. Am. Chem. Soc., 81, 2826 (1959), Tetrahedron Letters, No. 49, 4963, J. Am. Chem. Soc., 81, 2826–2829 (1959)).

The amount of the base is usually 1 to 30 moles, preferably 1.2 to 10 moles per one mole of the mixture of carbinol alkylates (3) and (R)-phenylhalogenomethylcarbinols The cyclization treatment is usually conducted in the presence of the solvent. Examples of the solvent include ethers such as tetrahydrofuran, diethyl ether, di-isopropyl ether, methyl-tert-butylether, etc.; aliphatic hydrocarbons such as pentane, hexane, heptane, etc.; aromatic hydrocarbons such as benzene, toluene, xylene, etc.; halogenated hydrocarbons such as dichloromethane, ethylene dichloride, chlorobenzene, etc.; ketones such as acetone, methyl ethyl ketone, methyl-i-butyl ketone, etc.; and a mixture thereof.

The amount of the solvent is usually 0.5 to 10 parts by weight, preferably 2 to 5 parts by weight per one part by weight of the mixture of the carbinol alkylates (3) and (R)-phenylhalogenomethylcarbinols (2).

The temperature is usually selected from −10° C. to boiling point of the solvent. For example, when 1 to 3N sodium hydroxide is used, the temperature is preferably about 0° to 20° C., more preferably about 0° to 5° C. when using potassium carbonate, the temperature is preferably about 30° to 100° C., more preferably about 40° to 60° C. Under these conditions, the carbinol alkylates (3) are not hydrolyzed, and not converted directly into styrene oxide, and only (R)-phenylhalogenomethylcarbinols (2) are selectively cyclized to form (R)-styrene oxides (1).

After the reaction, if necessary, the organic solvent is distilled off from the reaction mixture. Then, the resultant is extracted with hexane or the like, and hexane or the like is distilled off to obtain a mixture of carbinol alkylates (3) and styrene oxides (1).

In addition, styrene oxide (1) as the objective product can be easily obtained, for example, by subjecting the mixture to fractional distillation. For example, when the mixture of 3'-chlorostyrene oxide and an acetate ester of 3'-chlorophenyl-bromomethylcarbinol is distilled under reduced pressure at 3 mmHg, the former is distilled off at 3° C., while the latter is not distilled off until it is heated to 84° C. Therefore, the former can be separated, easily and efficiently, by distilling at 64° C. under 3 mmHg, while the latter is remained in a still pot.

The optical purity of the resulting (R)-styrene oxides (1) can be measured, for example, by subjecting to high performance chromatography with an optically active column.

Thus, the objective (R)-styrene oxides (1) having high optical purity can be obtained. Specific examples of compound (1) include (R) isomers of 3'-chlorostyrene oxide, 3'-bromostyrene oxide, 3'-fluorostyrene oxide, 3'-methylstyrene oxide, 3'-methoxystyrene oxide, 3'-trifluoromethylstyrene oxide, 4'-chlorostyrene oxide, 4'-bromostyrene oxide, 4'-fluorostyrene oxide, 4'-methylstyrene oxide, 4'-methoxystyrene oxide, 4'-trifluoromethylstyrene oxide, 2'-chlorostyrene oxide, 2'-bromostyrene oxide, 2'-fluorostyrene oxide, 2'-methylstyrene oxide, 2'-methoxystyrene oxide, 2'-trifluoromethylstyrene oxide, 3'-chloro-2'-methoxystyrene oxide, 3'-bromo-2'-methoxystyrene oxide, 3'-fluoro-2'-methoxystyrene oxide, 2'-methoxy-3'-methylstyrene oxide, 2',3'-dimethoxystyrene oxide, 3'-trifluoromethyl-2'-methoxy styrene oxide, 2',4'-dichlorostyrene oxide, 4'-bromo-2'-chlorostyrene oxide, 2'-chloro-4'-fluorostyrene oxide, 2',4'-methoxystyrene oxide, 2'-chloro-4'-methylstyrene oxide, 2'-chloro-4'-trifluoromethylstyrene oxide, 3'-chloro-5'-trifluoromethylstyrene oxide, 3'-bromo-5'-trifluoromethylstyrene oxide, 5'-trifluoromethyl-3'-fluorostyrene oxide, 5'-trifluoromethyl-3'-methylstyrene oxide, 5'-trifuoromethyl-3'-methoxystyrene oxide, 3',5'-ditrifluoromethylstyrene oxide, 3',5'-dichlorostyrene oxide, 3',5'-dibromostyrene oxide, 3',5'-difluorostyrene oxide, 2',4',6'-trifluorostyrene oxide, 2',4',6'-trichlorostyrene oxide, 2',4',6'-tribromostyrene oxide, 3',4'-methylenedioxystyrene oxide, etc. Among them, (R) isomers of 3'-chlorostyrene oxide, 3'-bromostyrene oxide, 3'-fluorostyrene oxide, 3'-methylstyrene oxide, 3'-methoxystyrene oxide, 3'-trifluoromethylstyrene oxide, etc. are preferred, and (R)-3'-chlorostyrene oxide is particularly preferred.

A process will now be described for producing phenyl-halogenomethylcarbinols (2) enriched with the (R) isomer comprising subjecting phenyl halogenomethyl ketones to asymmetric reduction.

Examples of the phenyl halogenomethyl ketones include the compounds represented by the formula (4):

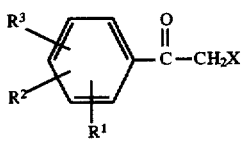

(4)

wherein $R^1$, $R^2$, $R^3$ and X are as defined above.

Specific examples of the phenyl halogenomethyl ketones (4) wherein X is a bromine atom include 2-bromo-3'-chloroacetophenone, 2-bromo-3'-bromoacetophenone, 2-bromo-3'-fluoroacetophenone, 2-bromo-3'-methylacetophenone, 2-bromo-3'-methoxyacetophenone, 2-bromo-3'-trifluoromethylacetophenone, 2-bromo-4'-chloroacetophenone, 2-bromo-4'-bromoacetophenone, 2-bromo-4'-fluoroacetophenone, 2-bromo-4'-methylacetophenone, 2-bromo-4'-methoxyacetophenone, 2-bromo-4'-trifluoromethylacetophenone, 2-bromo-2'-chloroacetophenone, 2-bromo-2'-bromoacetophenone, 2-bromo-2'-fluoroacetophenone, 2-bromo-2'-methylacetophenone, 2-bromo-2'-methoxyacetophenone, 2-bromo-2'-trifluoromethylacetophenone, 2-bromo-2'-chloro-3'-methoxyacetophenone, 2-bromo-2'-bromo-3'-methoxyacetophenone, 2-bromo-2'-fluoro-3'-methoxyacetophenone, 2-bromo-3'-methoxy-2'-methylacetophenone, 2-bromo-2',3'-dimethoxyacetophenone, 2-bromo-3'-methoxy-2'-trifluoromethylacetophenone, 2-bromo-2',3'-dichloroacetophenone, 2-bromo-2'-bromo-3'-chloroacetophenone, 2-bromo-3'-chloro-2'fluoroacetophenone, 2-bromo-3'-chloro-2'-methylacetophenone, 2-bromo-3'-chloro-2'-methoxyacetophenone, 2-bromo-3'-chloro-2'-trifluoromethylacetophenone, 2-bromo-2'-bromo-4'-chloroacetophenone, 2-bromo-2',4'-dibromoacetophenone, 2-bromo-2'-bromo-4'-fluoroacetophenone, 2-bromo-2'-bromo-4'-methylacetophenone, 2-bromo-2'-bromo-4'-methoxyacetophenone, 2-bromo-2'-bromo-4'-trifluoromethylacetophenone, 2-bromo-4'-chloro-2'-fluoroacetophenone, =-bromo-2',4'-difluoroacetophenone, 2-bromo-4'-bromo-2'-fluoroacetophenone, 2-bromo-2'-fluoro-4'-methylacetophenone, 2-bromo-2'-fluoro-4'-methoxyacetophenone, 2-bromo-2'-fluoro-4'-trifluoromethylacetophenone, 2-bromo-4'-chloro-2'-trifluoromethylacetophenone, 2-bromo-4'-bromo-2'-trifluoromethylacetophenone, 2-bromo-4'-fluoro-2'-trifluoromethylacetophenone, 2-bromo-4'-methyl-2'-trifluoromethylacetophenone, 2-bromo-4'-methoxy-2'-trifluoromethylacetophenone, 2-bromo-2',4'-ditrifluoromethylacetophenone, 2-bromo-4'-chloro-3'-trifluoromethylacetophenone, 2-bromo-4'-bromo-3'-trifluoromethylacetophenone, 2-bromo-4'-fluoro-3'-trifluoromethylacetophenone, 2-bromo-4'-methyl-3'-trifluoromethylacetophenone, 2-bromo-4'-methoxy-3'-trifluoromethylacetophenone, 2-bromo-3',4'-ditrifluoromethylacetophenone, 2-bromo-5'-bromo-3'-chloroacetophenone, 2-bromo-3',5'-dibromoacetophenone, 2-bromo-5'-bromo-3'-fluoroacetophenone, 2-bromo-5'-bromo-3'-methylacetophenone, 2-bromo-5'-bromo-3'-methoxyacetophenone, 2-bromo-3'-bromo-5'-trifluoromethylacetophenone, 2-bromo-3'-chloro-5'-trifluoromethylacetophenone, 2-bromo-3'-bromo-5'-trifluoromethylacetophenone, 2-bromo-3'-fluoro-5'-trifluoromethylacetophenone, 2-bromo-3'-methyl-5'-trifluoromethylacetophenone, 2-bromo-3'-methoxy-5'-trifluoromethylacetophenone, 2-bromo-3',5'-dimethoxyacetophenone, 2-bromo-3',5'-ditrifluoromethylacetophenone, 2-bromo-3',5'-dichloroacetophenone, 2-bromo-3',5'-dibromoacetophenone, 2-bromo-3',5'-difluoroacetophenone, 2-bromo-2',6'-dichloroacetophenone, 2-bromo-2',4',6'-trichloroacetophenone, 2-bromo-3',4',5'-trichloroacetophenone, 2-bromo-3',4'-methylenedioxyacetophenone, etc. When X is a chlorine atom, examples thereof include the above compounds wherein 2-bromo is replaced by 2-chloro.

The asymmetric reducing agent used in the asymmetric reduction of the phenyl halogenomethyl ketones (4) is not specifically limited, for example, there can be used an asymmetric reducing agent obtained from boranes and a β-amino alcohol, in which an absolute configuration of β-carbon is R, represented by the formula (5):

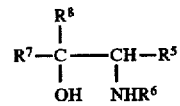

(5)

wherein $R^5$ is an alkyl group having 1 to 7 carbon atoms, a non-substituted or substituted aryl group, or a non-substituted or substituted aralkyl group; $R^6$ is a hydrogen atom, a lower alkyl group, or a non-substituted or substituted aralkyl group, or $R^5$ and $R^6$ together form a lower alkylene group; $R^7$ and $R^8$ independently indicate a hydrogen atom, an alkyl group having 1 to 7 carbon atoms, or a non-substituted or substituted aryl group, or $R^7$ and $R^8$ together form a lower alkylene group; or $R^7$ and $R^5$ together form a non-substituted or benzene ring-fused lower alkylene group, and/or obtained from the β-amino alcohol, a metal borohydride and an acid or a dialkylsufuric acid, or the like, industrially advantageously. Among them, it is preferred to use the latter asymmetric reducing agent using the metal borohydride.

Examples of the alkyl group having 1 to 7 carbon atoms for the substituent $R^5$ of β-amino alcohol (5) include a methyl group, ethyl group, n-propyl group, isopropyl group, n-butyl group, sec-butyl group, tert-butyl group, pentyl group, hexyl group, cyclohexyl group, etc. Examples of the non-substituted or substituted aryl group include a phenyl group, tolyl group, naphthyl group, etc. Examples of the non-substituted or substituted aralkyl group include benzyl group, phenethyl group, p-methylbenzyl group, etc.

Examples of the lower alkyl group for the $R^6$ include a methyl group, ethyl group, n-propyl group, isopropyl group, n-butyl group, sec-butyl group, tert-butyl group, etc. Examples of the non-substituted or substituted aralkyl include benzyl, phenethyl group, p-methylbenzyl group, etc. In addition, $R^6$ and $R^5$ may together form an alkylene group such as trimethylene group, tetramethylene group, pentamethylene group, etc.

Examples of the non-substituted or substituted aryl group in $R^7$ and $R^8$ include phenyl or naphthyl group optionally substituted with lower alkyl or lower alkoxy group, such as phenyl group, tolyl group, ethylphenyl group, n-propylphenyl group, isopropylphenyl group, n-butylphenyl group, i-butylphenyl group, dimethylphenyl group, methylethylphenyl group, diethylphenyl group, methylpropylphenyl group, methoxyphenyl group, ethoxyphenyl group, n-propoxyphenyl group, isopropoxyphenyl group, n-butoxyphenyl group, i-butoxyphenyl group, dimethoxyphenyl group, methoxyethoxyphenyl group, diethoxyphenyl group, methylmethoxyphenyl group, methylethoxyphenyl group, etc. Examples of the alkyl group having 1 to 7 carbon atoms include those which are the same as those described for $R^5$.

Examples of the lower alkylene group formed by $R^7$ and $R^8$ together include a tetramethylene group, pentamethylene group, hexamethylene group, etc. Examples of the non-substituted or substituted or benzene ring-fused lower alkylene group formed by $R^7$ and $R^8$ together include a trimethylene group, tetramethylene group, pentamethylene group, o-phenylenemethylene group, o-phenylenedimethylene group, etc.

Examples of the 5-amino alcohol (5) wherein the absolute configuration of β-carbon is R include (R)-valinol((R)-(+)-2-amino-3-methylbutane-2-ol), (R)-alaninol((R)-(−)-2-aminopropane-1-ol), (R)-leucinol ((R)-(−)-2-amino-4-methyl-pentane-1-ol), (R)-phenylalanionol((R)-(−)-2-amino-3-phenylpropane-1-ol), (R)-phenylglycinol((R)-(−)-2-amino-2-phenylethane-1-ol), (R)-prolinol((R)-(−)-2-pyrrolidinemethanol), (R)-cyclohexylalaninol, (1S,2R)-1-phenyl-2-amino-1-propanol, (1S,2R)-1-(2,5-dimethylphenyl)-2-amino-1-propanol, (1S,2R)-1-(2,5-dimethoxyphenyl)-2-amino-1-propanol, (1S,2R)-1-(2,5-diethoxyphenyl)-2-amino-1-propanol, (1S,2R)-1-(2,5-dipropoxyphenyl)-2-amino-1-propanol, (1S,2R)-1-(2-methoxyphenyl)-2-amino-1-propanol, (1S,2R)-1-(2-ethoxyphenyl)-2-amino-1-propanol, (1S,2R)-1-(2-propoxyphenyl)-2-amino-1-propanol, (1S,2R)-1-(2-methoxy-5-methylphenyl)-2-amino-1-propanol, (1S,2R)-1-(4-methoxy-2-methylphenyl)-2-amino-1-propanol, (1S,2R)-1-(2-ethoxy-5-methylphenyl)-2-amino-1-propanol, (1S,2R)-1-(2,4-dimethylphenyl)-2-amino-1-propanol, (1S,2R)-1-(2,4,6-trimethylphenyl)-2-amino-1-propanol, (1S,2R)-2-amino-1,2-diphenylethanol, (R)-2-amino-1,1,3-triphenylpropanol, (R)-1-(1'-amino-2'-phenylethyl)cyclopentanol, (R)-2-amino-1,1,2-triphenylethanol, (R)-1-(1'-amino-1'-phenylmethyl)cyclopentanol, (R)-2-amino-1,1-diphenylpropanol, (R)-2-amino-3-methyl-1,1-diphenylbutane-1-ol, (R)-2-amino-3-methyl-1,1-diphenylpentane-1-ol, (R)-2-amino-4-methyl-1,1-diphenylpentanol, (R)-2-amino-4-methylthio-1,1-diphenylbutanol, (R)-α,α-diphenyl-2-pyrrolidinemethanol, (1S,2R)-2-aminocyclopentan-1-ol, (1R,2S)-1-aminoindan-2-ol, (R)-1-(1-amino-2-phenylethyl)cyclopentanol, (R)-1-(1-amino-1-phenylmethyl)cyclopentanol, (1S,2R)-2-aminocyclopentan-1-ol, etc.; or N-alkyl- and N-aralkyl-substituted products thereof. Some of these are commercially available, but they can be derived from an optically active amino acid or produced by the process described in J. Org. Chem., 25, 1929 (1960), J. Am. Chem. Soc., 52, 3317 (1930), J. Am. Chem. Soc., 51, 2262, (1929), J. Org. Chem., 11, 390 (1946).

The amount of β-amino alcohol (5) is usually 0.005 to 0.5 moles, preferably 0.01 to 0.4 moles per one mole of the phenyl halogenomethyl ketones (4).

Examples of the boranes include diborane ($B_2M_6$), tetraborane ($B_4H_{10}$), hexaborane ($B_6H_{10}$), tetrahydrofuran (THF)-borane complex, dimethyl sulfide-borane complex, cathecol borane, etc. The amount of these boranes are usually 0.3 to 2 moles, preferably 0.5 to 1.5 moles (in terms of boron) per one mole of the phenyl halogenomethyl ketones (4).

Examples of the metal borohydride include lithium borohydride, sodium borohydride, potassium borohydride, zinc borohydride, etc. The amount of the metal borohydride is usually a 0.3 to 2 moles, preferably 0.6 to 1.5 moles (in terms of boron) per one mole of the phenyl halogenomethyl ketones (4).

Examples of the acid include Bronsted acids such as hydrogen chloride, sulfuric acid, acetic acid, phosphoric acid, methanesulfonic acid, p-toluenesulfonic acid, etc.; Lewis acids such as zinc chloride, boron trifluoride, aluminum chloride, aluminum bromide, titanium tetrachloride, tin tetrachloride, tin dichloride, etc. The amount of the acid is usually about 0.5 to 2.5 equivalents, preferably about 0.8 to 2.2 equivalents per one equivalent of the metal borohydride.

Examples of the dialkyl sulfate include lower dialkyl sulfates such as dimethyl sulfate, diethyl sulfate, etc. The amount of the dialkyl sulfate is usually 0.9 to 1.1 moles, preferably 0.95 to 1.05 moles, per one mole of the metal borohydride.

A solvent is usually used for preparing an asymmetric reducing agent from the β-amino alcohol (5) and boranes, and the asymmetric reducing agent is prepared by mixing them in the solvent.

Examples of the solvent include ethers such as tetrahydrofuran, 1,3-dioxane, 1,4-dioxane, 1,3-dioxolane, thioxane, ethylene glycol dimethyl ether, diethylene glycol dimethyl ether, methyl tert-butyl ether, etc.; aromatic hydrocarbons such as benzene, toluene, xylene, chlorobenzene, etc.; hydrocarbons such as hexane, heptane, cyclohaxane, etc.; halogenated hydrocarbons such as methylene dichloride, ethylene chloride, carbon tetrachloride, etc. The amount of the solvent is usually 0.5 to 50 parts by weight per one part of the β-amino alcohol (5).

The preparation temperature is usually about −20° to 80° C., preferably about 0° to 60° C.

In addition, preparation of the asymmetric reducing agent from the β-amino alcohol (5), metal borohydride and acid or dialkyl sulfate is carried out in a solvent.

Examples of such solvent include ethers such as dioxane, tetrahydrofuran, diglyme, triglyme, 1,3-dioxolane, etc.; sulfides such as dimethyl sulfide, diethyl sulfide, etc.; or a mixture thereof, or a mixture of these solvents or a mixture thereof and hydrocarbons such as benzene, toluene, xylene, chlorobenzene, 1,2-dichloroethane, etc. The amount of the solvent is usually about 1 to 50 parts by weight per one mole of the 5-amino alcohol (5).

The asymmetric reducing agent is prepared, for example, by adding an acid or dialkyl sulfate to a mixture of the β-amino alcohol (5), metal borohydride and solvent, or by adding the acid or dialkyl sulfate to a mixture of the metal borohydride and solvent and then adding amino alcohol (5). In these cases, the acid or the dialkyl sulfate may be added as a mixture with the solvent. It can also be prepared by adding a mixture of the metal borohydride and the solvent to a mixture of the β-amino alcohol (5), acid and solvent.

The preparation temperature of the asymmetric reducing agent is usually about −20° to 100° C., preferably about 0° to 80° C.

When the phenyl halogenomethyl ketones (4) are reduced with the asymmetric reducing agent thus obtained, the asymmetric reducing agent may be isolated but is usually used as it is.

The amount of the asymmetric reducing agent is usually 0.005 to 0.5 mole, preferably 0.01 to 0.4 mole (in terms of the β-amino alcohol), per one mole of the phenyl halogenomethyl ketones (4).

The reduction is usually conducted by adding the phenyl halogenomethyl ketones (4) or a mixture of this compound (4) and solvent to a mixture of the asymmetric reducing agent and solvent, or by adding a mixture of asymmetric reducing agent and solvent to a mixture of the phenyl halogenomethyl ketones (4) and solvent.

Examples of the solvent of the phenyl halogenomethyl ketones (4) include the same solvents as those described in the preparation step of the asymmetric reducing agent. When using the solvent, the amount of the solvent is usually 0.1 to 20 parts by weight, preferably 1 to 18 parts by weight, per one part by weight of the phenyl halogenomethyl ketones (4).

The reducing temperature is usually about −76° to 100° C., preferably about 10° to 80° C.

The phenylhalogenomethylcarbinols (2) enriched with (R) isomer is thus formed. The carbinol (2) can be easily isolated, for example, by adding an acid (e.g. hydrochloric acid, etc.) to a reaction mass to decompose the reducing agent, optionally distilling off the solvent, adding an aqueous solution of an extraction solvent (e.g. toluene, etc.) and an acid (e.g. hydrochloric acid, etc.) to remove a salt of the β-amino alcohol (5) and acid in the aqueous layer and distilling off the solvent of the separated organic layer.

In addition, the β-amino alcohol (5) can be recovered by alkalifying the aqueous layer, extracting with an extraction solvent (e.g. toluene, etc.) and distilling off the solvent.

The phenylhalogenomethylcarbinols (2) enriched with (R) isomer can also be further purified by subjecting to purification means such as distillation, various chromatographies, etc.

As the phenyl halogenomethyl ketones (4) as one of the raw material of the above phenylhalogenomethylcarbinols (2), those produced by any processes can be used. Particularly, phenyl bromomethyl ketones wherein X is bromine can be produced by the following process, industrially advantageously.

That is, a process for producing phenyl bromomethyl ketones can comprise reacting acetophenones represented by the formula (6):

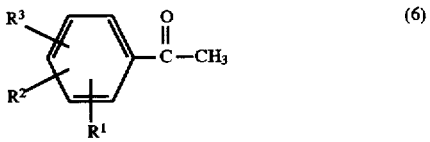

wherein $R^1$, $R^2$ and $R^3$ are as defined above, with bromine in an alcohol solvent.

Specific examples of the acetophenones (6) include 3'-chloroacetophenone, 3'-bromoacetophenone, 3'-fluoroacetophenone, 3'-methylacetophenone, 3'-methoxyacetophenone, 3'-trifluoromethylacetophenone, 4'-chloroacetophenone, 4'-bromoacetophenone, 4'-fluoroacetophenone, 4'-methylacetophenone, 4'-methoxyacetophenone, 4'-trifluoromethylacetophenone, 2'-chloroacetophenone, 2'-bromoacetophenone, 2'-fluoroacetophenone, 2'-methylacetophenone, 2'-methoxyacetophenone, 2'-trifluoromethylacetophenone, 2'-chloro-3'-methoxyacetophenone, 2'-bromo-3'-methoxyacetophenone, 2'-fluoro-3'-methoxyacetophenone, 3'-methoxy-2'-methylacetophenone, 2',3'-dimethoxyacetophenone, 3'-methoxy-2'-trifluoromethylacetophenone, 2',3'-dichloroacetophenone, 2'-bromo-3'-chloroacetophenone, 3'-chloro-2'-fluoroaetophenone, 3'-chloro-2'-methylacetophenone, 3'-chloro-2'-methoxyacetophenone, 3'-chloro-2'-trifluoromethylacetophenone, 2'-bromo-4'-chloroacetophenone, 2',4'-dibromoacetophenone, 2'-bromo-4'-fluoroacetophenone, 2'-bromo-4'-methylacetophenone, 2'-bromo-4'-methoxyacetophenone, 2'-bromo-4'-trifluoromethylacetophenone, 4'-chloro-2'-fluoroacetophenone, 2',4'-difluoroacetophenone, 4'-bromo-2'-fluoroacetophenone, 2'-fluoro-4'-methylacetophenone, 2'-fluoro-4'-methoxyacetophenone, 2'-fluoro-4'-trifluoromethylacetophenone, 4'-chloro-2'-trifluoromethylacetophenone, 4'-bromo-2'-trifluoromethyacetophenone, 4'-fluoro-2'-trifluoromethylacetophenone, 4'-methyl-2'-trifluoromethylacetophenone, 4'-methoxy-2'-trifluoromethylacetophenone, 4',2'-ditrifluoromethylacetophenone, 4'-chloro-3'-trifluoromethylacetophenone, 4'-bromo-3'-trifluoromethylacetophenone, 4'-fluoro-3'-trifluoromethylacetophenone, 3'-trifluoromethyl-4'-methylacetophenone, 3'-trifluoromethyl-4'-methoxyacetophenone, 3',4'-ditrifluoromethylacetophenone, 5'-bromo-3'-chloroacetophenone, 3',5'-dibromoacetophenone, 5'-bromo-3'-fluoroacetophenone, 5'-bromo-3'-methylacetophenone, 5'-bromo-3'-methoxyacetophenone, 5'-bromo-3'-trifluoromethylacetophenone, 3'-chloro-5'-trifluoromethylacetophenone, 3'-bromo-5'-trifluoromethylacetophenone, 3'-fluoro-5'-trifluoromethylacetophenone, 3'-methyl-5'-trifluoromethylacetophenone, 3'-methoxy-5'-trifluoromethylacetophenone, 3',5'-dimethoxyacetophenone, 3',5'-ditrifluoromethylacetophenone, 3',5'-dichloroacetophenone, 3',5'-dibromoacetophenone, 3',5'-difluoroacetophenone, 2',6'-dichloroacetophenone, 2',4',6'-trichloroacetophenone, 3',4',5'-trichloroacetophenone, 3',4'-methylenedioxyacetophenone, etc.

Commercially available bromine can be used as it is. The amount of bromine is usually 0.8 to 0.99 mole per one mole of the acetophenones (6). When it is less than 0.8 mole, the yield is decreased. On the other hand, when it exceeds 0.99 mole, dibromoacetophenone is formed as by-product.

Examples of the alcohol solvent include lower alcohols such as methanol, ethanol, propanol, etc. Among them, methanol is preferred. It is preferred to use the alcohol solvent after drying with molecular sieves 4A, etc..

The amount of the alcohol solvent is 0.5 to 20 parts by weight, preferably 1.5 to 10 parts by weight, per one part by weight of the acetophenones (6).

The bromination reaction is usually conducted by adding dropwise bromine to a mixture of the acetophenones (6) and the alcohol solvent. In the bromination reaction of a dialkyl ketone, it has been known that adding dropwise bromine is not preferred and bromine must be added in one portion (Organic Synthesis, VI, 194 (1988)). However, it is preferred to add dropwise in the present invention.

The dropping temperature is usually about 30° to 45° C. In the case of the dialkyl ketone, the reaction is conducted while maintaining at 10° C. or less. In this reaction, the temperature is preferably about 30° to 45° C. When the temperature is less than 30° C., it takes a long time to complete the reaction. On the other hand, when the temperature exceeds 45° C., by-product is formed.

A ketal is formed by the bromination reaction, and the ketal is hydrolyzed by adding water in the amount which is almost the same as that of the alcohol solvent. The dialkyl ketone is hydrolyzed by adding concentrated sulfuric acid. In the present invention, the reaction sufficiently proceeds without adding sulfuric acid.

The formed phenyl bromomethyl ketones can be isolated by adding water in the amount at least that of the acetophenones (6) to the reaction mixture, cooling and filtering the precipitated crystals. If necessary, the resulting objective product can also be purified by recrystallizing from hexane, heptane, isopropanol, etc.

According to the present invention, the objective (R)-styrene oxides (1) can be efficiently produced in high optical purity.

The following Examples and Comparative Examples further illustrate the present invention in detail but are not to be construed to limit the scope thereof.

EXAMPLE 1

(R)-Bromomethyl-3'-chlorophenylcarbinol (optical purity: 91% ee, 29.2 g), vinyl acetate (89.2 g), hexane (288 g) and Lipase QL (5.3 g, manufactured by Meito Sangyo Co., Ltd.) were charged in a 1 liter four-necked flask equipped with a stirrer, a thermometer and a condenser under a nitrogen atmosphere. After stirring at 50° C. for 4 hours, the mixture was cooled to 10° C. and Lipase QL was removed by filtration, and then the filtrate was concentrated under reduced pressure to obtain an oily mixture. The amount of (R)-bromomethyl-3'-chlorophenylcarbinol contained in the resulting mixture was measured by subjecting to high performance liquid chromatography [solvent: hexane/1,2-dichloroethane/ethanol=(400:40:1)] with an optically active column (OA-2500I). As a result, the amount was 26.0 g and the optical purity was 100% ee. The optical purity of 100% ee means that the amount of the (S)-form is less than the detection limit.

This mixture was dissolved in hexane (104 ml) and THF (26 ml) and the resulting solution was charged in a 1 liter four-necked flask equipped with a stirrer, a thermometer and a condenser, followed by cooling to 5° C. To the mixture, an aqueous 2N sodium hydroxide (166 g) was added dropwise over 30 minutes while cooling to 1° to 5° C. After stirring with maintaining at the same temperature for 30 minutes, the hexane layer was separated. The aqueous layer was extracted with hexane (60 ml). After combining the hexane layers, the combined layer was washed four times with water (60 ml). After the resultant was dried over anhydrous magnesium sulfate and filtered, the filtrate was concentrated. The amount of (R)-3'-chlorostyrene oxide contained in the resulting mixture was measured by subjecting to high performance liquid chromatography [solvent: hexane/1,2-dichloroethane/ethanol=(500:5:0.025)] with an optically active column (OA-2500I). As a result, the amount was 14.9 g. The optical purity was 100% ee. That is, the amount of (S)-3'-chlorostyrene oxide was less than the detection limit.

The resulting residue was distilled at 63° C. under 3 mmHg to obtain (R)-3'-chlorostyrene oxide [initial distillate: 2.2 g (chemical purity: 98%, optical purity: 100% ee), main distillate: 8.1 g (chemical purity: 100%, optical purity: 100% ee), post main distillate: 3.3 g (chemical purity: 100%, optical purity: 100% ee).

EXAMPLE 2

According to the same manner as that described in Example 1 except for using (R)-bromomethyl-3'-chlorophenylcarbinol (optical purity: 89.8% ee, 30 g), vinyl chloroacetate (15 g) (in place of vinyl acetate), hexane (450 ml) and Lipase QL (15 g, manufactured by Meito Sangyo Co., Ltd.) and stirring at 43° C. for 7 hours, the mixture was subjected to a lipase treatment, filtered and then concentrated to obtain an oily mixture. The amount of (R)-bromomethyl-3'-chlorophenylcarbinol contained in the mixture was 25.1 g and the optical purity was 100% ee.

According to the same manner as that described in Example 1 except for dissolving this mixture in hexane (100 ml) and THF (25 ml), the solution was treated with aqueous sodium hydroxide, and then subjected to a post treatment. The amount of (R)-3'-chlorostyrene oxide contained in the residue was 15.1 g. The resulting residue was distilled at 63° C. under 3 mmHg to obtain 13.8 g of (R)-3'-chlorostyrene oxide (chemical purity: 99.8%, optical purity: 100% ee).

The yield of (R)-3'-chlorostyrene oxide (optical purity: 100% ee) was 74.5% based on (R)-3'-chlorophenylcarbinol (optical purity: 89.8% ee).

EXAMPLE 3

According to the same manner as that described in Example 1 except for using (R)-bromomethyl-3'-chlorophenylcarbinol (optical purity: 89.8% ee, 30 g), isopropenyl acetate (150 g) (in place of vinyl acetate), hexane (450 ml) and Lipase QL (15 g, manufactured by Meito Sangyo Co., Ltd.) and stirring at 43° C. for 4 hours, the mixture was subjected to a lipase treatment, filtered and then concentrated to obtain an oily mixture. The amount of (R)-bromomethyl-3'-chlorophenylcarbinol contained in the mixture was 27.0 g and the optical purity was 100% ee.

According to the same manner as that described in Example 1 except for dissolving this mixture in hexane (100 ml) and THF (25 ml) and using an aqueous 2N sodium hydroxide solution (160 g), the solution was treated with aqueous sodium hydroxide and then subjected to a post treatment. The amount of (R)-3'-chlorostyrene oxide contained in the resulting residue was 16.0 g and the optical purity was 100% ee.

The resulting residue was distilled at 63° C. under 3 mmHg to obtain 14.2 g of (R)-3'-chlorostyrene oxide (chemical purity: 99.8%, optical purity: 100% ee).

The yield of (R)-3'-chlorostyrene oxide (optical purity: 100% ee) was 76.2% based on (R)-bromomethyl-3'-chlorophenylcarbinol (optical purity: 89.8% ee).

EXAMPLE 4

According to the process described in J. Chem. Soc. Perkin Trans. I, 1985, 2039–2044, (R)-valinol((R)-(−)-2-amino-3-methylbutan-1-ol) was synthesized from (R)-valine.

After a four-necked flask equipped with a stirrer, a thermometer and a condenser was charged with nitrogen, the above (R)-valinol (2.64 g, 25.7 mmol) and THF (600 ml) dried with molecular sieves were charged.

Then, THF BH₃ solution (1M, 282 ml) was added using a syringe and, after heating to 45° to 50° C. with stirring, the mixture was maintained at the same temperature for 90 minutes to prepare an symmetric reducing agent.

Then, a mixture of 2-bromo-3'-chloroacetophenone (30 g, 128.4 mmol) and THF (600 ml) dried with molecular sieves was added dropwise over 90 minutes while maintaining the same temperature. The mixture was maintained at the same temperature for 10 minutes. After cooling to 10° C., a solution prepared by diluting concentrated hydrochloric acid with ethanol (1 molar concentration, 60 ml) was added over 20 minutes.

After the solvent was distilled off, toluene (800 g) was added and aqueous 7% hydrochloric acid (600 g) was further added, followed by phase separation. Aqueous 7% hydrochloric acid (600 g) was added again to the toluene layer, followed by phase separation and further washing with water (600 g). The oil layer was dried over anhydrous magnesium sulfate, filtered, and then washed with toluene (100 g). After the filtrate and the wash were combined, the solvent was distilled off to obtain 27.9 g of (R)-bromomethyl-3'-chlorophenylcarbinol. The yield was 93% and the optical purity was 90% ee.

According to the same manner as that described in Example 1 except for using (R)-bromomethyl-3'-chlorophenylcarbinol (25 g), vinyl acetate (100 g), hexane (300 g) and Lipase QL (15 g, manufactured by Meito Sangyo Co., Ltd.) and stirring at 35° C. for 1.5 hours, the mixture was subjected to a lipase treatment, filtered and then concentrated to obtain an oily mixture. The amount of (R)-bromomethyl-3'-chlorophenylcarbinol contained in the mixture was 23.0 g and the optical purity was 100% ee.

According to the same manner as that described in Example 1 except for dissolving this mixture in hexane (100 ml) and THF (25 ml) and using an aqueous 2N sodium hydroxide solution (160 g), the solution was treated with aqueous sodium hydroxide and then subjected to a post treatment.

The resulting residue was distilled at 63° C. under 3 mmHg to obtain 10.9 g of (R)-3'-chlorostyrene oxide (chemical purity: 99.8%, optical purity: 100% ee).

The yield of (R)-3'-chlorostyrene oxide (optical purity: 100% ee) was 70% based on (R)-bromomethyl-3'-chlorophenylcarbinol (optical purity: 90% ee).

EXAMPLE 5

Under a nitrogen atmosphere, 3'-chloroacetophenone (154.6 g, 1 mol) and anhydrous methanol (310 ml) dried with molecular sieves were charged in a four-necked flask. Bromine (158.2 g, 0.99 mol) was added dropwise with stirring at a temperature in a range from 30° to 45° C. over one hour, and the mixture was maintained at the same temperature for 10 minutes.

After water (160 g) was added, the solution was cooled to −10° C. to precipitate crystals which were filtered to obtain 250 g of a crude cake. This crude cake was dissolved in heptane (750 g), and the solution was washed twice with water (200 g), dried over anhydrous magnesium sulfate, filtered, washed and then concentrated to obtain 212.5 g of 2-bromo-3'-chloroacetophenone. The yield was 91.0% and no impurity was detected.

According to the same manner as that described in Example 4 except for using (R)-phenylglycinol (4.66 g, 34 mmol) (in place of (R)-valinol), THF (50 ml) and THF BH$_3$ solution (1M, 282 ml), an asymmetric reducing agent was prepared.

According to the same manner as that described in Example 4 except for adding a mixture of the above 2-bromo-3'-chloroacetophenone (40 g, 0.171 mol) and THF (800 ml) over 130 minutes and adding a concentrated hydrochloric acid-ethanol solution (80 ml), the mixture was reduced and subjected to a post treatment to obtain 37.9 g of (R)-bromomethyl-3'-chlorophenylcarbinol. The yield was 94% and the optical purity was 92% ee.

According to the same manner as that described in Example 4 except for using (R)-bromomethyl-3'-chlorophenylcarbinol (30 g), vinyl acetate (90 g), hexane (270 g) and Lipase QL (5.5 g, manufactured by Meito Sangyo Co., Ltd.) and stirring at 35° C. for 4 hours, the mixture was subjected to a lipase treatment, filtered and then concentrated to obtain an oily mixture. The amount of (R)-bromomethyl-3'-chlorophenylcarbinol contained in the mixture was 27.9 g and the optical purity was 100% ee.

According to the same manner as that described in Example 4 except for using this mixture and using an aqueous 2N sodium hydroxide solution (150 g), the solution was treated with an aqueous sodium hydroxide and then subjected to a post treatment.

The resulting residue was distilled at 63° C. under 3 mmHg to obtain 14.4 g of (R)-bromomethyl-3'-chlorostyrene oxide (chemical purity: 99.8%, optical purity: 100% ee).

The yield of (R)-3'-chlorostyrene oxide (optical purity: 100% ee) was 72.5% based on (R)-3'-chlorophenylcarbinol (optical purity: 92% ee).

EXAMPLE 6

According to the same manner as that described in Example 4 except for using (1S,2R)-(+)-norephedrine (6.4 g, 42.4 mmol) (in place of (R)-valinol), THF (40 ml) and THF BH3 solution (1M, 256 ml), an asymmetric reducing agent was prepared.

According to the same manner as that described in Example 4 except for adding a solution of 3'-chlorophenacyl chloride (40 g, 211.6 mmol) and THF (800 ml) over 120 minutes while maintaining at 50 to 55° C. and adding a concentrated hydrochloric acid-ethanol solution (280 ml), the mixture was reduced and subjected to a post treatment to obtain 37.2 g of (R)-chloromethyl-3'-chlorophenylcarbinol 1. The yield was 93% and the optical purity was 91% ee.

According to the same manner as that described in Example 4 except for using this (R)-chloromethyl-3'-chlorophenylcarbinol (34 g), vinyl acetate (392 ml), hexane (1300 ml) and Lipase QL (34 g, manufactured by Meito Sangyo Co., Ltd.) and stirring at 50° to 55° C. for 2 hours, the mixture was subjected to a lipase treatment, filtered and then concentrated to obtain an oily mixture. The amount of (R)-chloromethyl-3'-chlorophenylcarbinol contained in the mixture was 31 g and the optical purity was 100% ee.

According to the same manner as that described in Example 4 except for using this mixture and using aqueous 2N sodium hydroxide solution (510 g), the solution was treated with an aqueous sodium hydroxide and then subjected to a post treatment.

The resulting residue was distilled at 63° C. under 3 mmHg to obtain 15.9 g of (R)-3'-chlorostyrene oxide (chemical purity: 99.8%, optical purity: 100% ee).

The yield of (R)-3'-chlorostyrene oxide (optical purity: 100% ee) was 74.5% based on (R)-chloromethyl-3'-chlorophenylcarbinol (optical purity: 91% ee).

EXAMPLE 7

According to the same manner as that described in Example 1 except for using (R)-chloromethyl-3'-chlorophenylcarbinol (optical purity: 92% ee, 25 g), vinyl acetate, (90 g), hexane (300 g) and Lipase QL (25 g, manufactured by Meito Sangyo Co., Ltd.) and stirring at 50° C. for 3 hours, the mixture was subjected to a lipase treatment, filtered and then concentrated to obtain an oily mixture. The amount of (R)-chloromethyl-3'-chlorophenylcarbinol contained in the mixture was 22 g and the optical purity was 100% ee.

This mixture, acetone (1000 ml) and potassium carbonate (200 g) were charged in a flask equipped with a stirrer, a thermometer and a condenser, and the mixture was heated with stirring. The mixture was reacted with maintaining at the temperature where acetone is refluxed for 3.5 hours. After cooling to 10° C., acetone was distilled off under reduced pressure. Hexane (400 ml) and then water (400 ml) were added to the residue to dissolve potassium carbonate. Then, the hexane layer was collected by phase separation and washed three times with water (100 ml). The resultant hexane layer was dried over anhydrous magnesium sulfate and filtered, and then the filtrate was concentrated.

The resulting residue contained 15.7 g of (R)-3'-chloroetyrene oxide. The optical purity was 100% ee.

The resulting residue was distilled at 63° C. under 3 mmHg to obtain (R)-3'-chlorostyrene oxide [initial distillate: 4.5 g (chemical purity: 95%, optical purity: 100% ee), main distillate: 5.6 g (chemical purity: 100%, optical purity: 100% ee), post main distillate: 3.2 g (chemical purity: 100%, optical purity: 100% ee).

The yield of (R)-3'-chlorostyrene oxide (optical purity: 100% ee) was 67.8% based on (R)-chloromethyl-3'-chlorophenylcarbinol (optical purity: 92% ee).

EXAMPLE 8

After a four-necked flask equipped with a stirrer, a thermometer and a condenser was substituted with nitrogen, (1S,2R)-(+)-norephedrine (1.53 g), THF (386 ml) and sodium borohydride (7.76 g) were charged. After heating to 57° C., a mixture of dimethyl sulfate (25.9 g) and THF (100 ml) was added at 57° to 58° C. over 70 minutes, followed by stirring at the same temperature for 3 hours to prepare a reducing agent.

Then, a mixed solution of α-bromo-3',4'-methylenedioxy acetophenone (78.7 g) and THF (157 g) was added at the same temperature over 90 minutes, followed by stirring at the same temperature for 10 minutes. 7% hydrochloric acid (200 ml) was added and, after stirring for one hour, the mixture was neutralized with an aqueous 8% sodium hydroxide solution.

The THF layer was separated and the aqueous layer was extracted with toluene (100 ml). Then, the THF layer and toluene layer were combined, and the mixture was concentrated under reduced pressure. After the resulting solid was dissolved in toluene (600 g), the solution was washed twice with 7% hydrochloric acid (200 ml), washed with saturated sodium chloride solution, dried over anhydrous magnesium sulfate, and then filtered. The filtrate was concentrated to obtain 63.6 g of a solid containing (R)-bromomethyl-3',4'-methylenedioxyphenylcarbinol. The optical purity was 87.8% ee.

Then, this solid (68 g) containing (R)-bromomethyl-3',4'-methylenedioxyphenylcarbinol, toluene (136 g), BHT (50 mg), vinyl acetate (14 ml) and Lipase QL (4 g, manufactured by Meito Sangyo Co., Ltd.) were charged in a flask under a nitrogen atmosphere and, after stirring at 58° to 59° C. for 20.5 hours, the mixture was filtered and washed. Then, the filtrate was concentrated to obtain 55.2 g of a solid containing (R)-bromomethyl-3',4'-methylenedioxyphenylcarbinol. The optical purity was 100% ee.

Aqueous 8% sodium hydroxide (618 ml) was added to a solution consisting of toluene (270 g) and a mixture (90 g) of the above solid and a solid obtained according to the same manner as that described above, over 2 hours while maintaining at 4° to 5° C. Then, the mixture was stirred at the same temperature for 3 hours and the toluene layer was collected. After the aqueous layer was extracted twice with toluene (300 g), the toluene layer and the extracted toluene were combined. The mixture was washed with saturated sodium chloride solution, dried over anhydrous magnesium sulfate, and then filtered and washed. After the wash and the filtrate were combined, the mixture was concentrated to obtain a 71.6 g of an oily product containing (R)-3',4'-methylenedioxystyrene oxide (optical purity: 100% ee).

Then, this oily product (10 g) was distilled at 110° C. under 0.18 mmHg to obtain 4.2 g of (R)-3',4'-methylenedioxy styrenes oxide (chemical purity: 95%, optical purity: 100% ee).

EXAMPLE 9

According to the same manner as that described in Example 8 except for charging (1S,2R)-(+)-norephedrine (1.4 g), THF (384 ml) and sodium borohydride (7.71 g), heating to 47° C., adding a mixed solution of dimethyl sulfate and THF at a temperature in a range from 47° to 63° C. over 80 minutes and stirring at 60° to 62° C. for 3 hours, a reducing agent was prepared.

According to the same manner as that described in Example 8 except for adding a mixed solution of α-bromo-4'-chloroacetophenone (75 g) and THF (157 g) at the same temperature over 140 minutes and stirring at the same temperature for 10 minutes, the mixture was reduced and subjected to a post treatment to obtain 82.6 g of an oily product containing (R)-bromomethyl-4'-chlorophenylcarbinol. The optical purity was 70% ee.

According to the same manner as that described in Example 8 except for using this oily product (79.2 g), toluene (150 g), BHT (250 mg), vinyl acetate (15 ml) and Lipase QL (3.75 g, manufactured by Meito Sangyo Co., Ltd.) and stirring at 55° to 60° C. for 19 hours, the mixture was subjected to a lipase treatment and a post treatment to obtain 78.2 g of an oily product containing (R)-bromomethyl-4'-chlorophenylcarbinol. The optical purity was 100% ee.

According to the same manner as that described in Example 8 except for using a mixture of this oily product (77 g) and toluene (231 g), adding aqueous 8% sodium hydroxide (385 g) over 40 minutes and stirring for one hour, the solution was subjected to a sodium hydroxide treatment and a post treatment to obtain 60.4 g of an oily product containing (R)-4'-chlorostyrene oxide. The optical purity was 100% ee.

Then, the resulting residue was distilled at 65° C. under 0.6 mmHg to obtain 15.4 g of (R)-4'-chlorostyrene oxide (chemical purity: 96%, optical purity: 100% ee).

EXAMPLE 10

According to the same manner as that described in Example 8 except for using (1S,2R)-(+)-norephedrine (0.99 g), THF (320 g) and sodium borohydride (5.16 g), heating to 55° C., adding dimethyl sulfate (17.18 g) at a temperature in a range from 55° to 60° C. over 60 minutes and stirring at 60° to 62° C. for 3 hours, a reducing agent was prepared.

According to the same manner as that described in Example 8 except for adding a mixed solution of α-bromo-3'-methoxyacetophenone (50 g) and THF (80 ml) over 60 minutes and stirring at the same temperature for 10 minutes, the mixture was reduced and subjected to a post treatment to obtain 51 g of an oily product containing (R)-bromomethyl-3'-methoxyphenylcarbinol. The optical purity was 72% ee.

According to the same manner as that described in Example 8 except for using this oily product (50 g), toluene (100 g), BHT (100 mg), vinyl acetate (10 ml) and Lipase QL (7.5 g, manufactured by Meito Sangyo Co., Ltd.) and stirring at a temperature in a range from 55° to 60° C. for 19 hours, the mixture was subjected to a lipase treatment and a post treatment to obtain 51 g of an oily product containing (R)-bromomethyl-3'-methoxyphenylcarbinol. The optical purity was 100% ee.

According to the same manner as that described in Example 8 except for using a mixture of this oily product (46.8 g) and toluene (164 g), adding aqueous 9.5% sodium hydroxide (197 g) over 30 minutes and stirring for one hour, the solution was subjected to a sodium hydroxide treatment and a post treatment to obtain 37.6 g of an oily product containing (R)-3'-methoxystyrene oxide (optical purity: 100% ee).

Then, the resulting residue was distilled at 77° C. under 0.38 mmHg to obtain 18.8 g of (R)-3'-methoxystyrene oxide (chemical purity: 99.2%, optical purity: 100% ee).

EXAMPLE 11

According to the same manner as that described in Example 1 except for using vinyl acetate (5.5 g), Lipase QL (3.2 g) and BHT (200 mg) in place of vinyl acetate (89.2 g) and Lipase QL (5.3 g), the mixture was subjected to a lipase treatment, filtered and then concentrated to obtain an oily mixture. The amount of (R)-bromomethyl-3'-chlorophenylcarbinol contained in the mixture was 26.2 g and the optical purity was 100% ee.

According to the same manner as that described in Example 1, this mixture was treated with aqueous sodium hydroxide and subjected to a post treatment. The amount of (R)-3'-chlorostyrene oxide contained in the residue was 15 g.

According to the same manner as that described in Example 1, the resulting residue was distilled to obtain (R)-3'-chlorostyrene oxide [initial distillate: 2 g (chemical purity: 98%, optical purity: 100% ee), main distillate: 11.4 g (chemical purity: 100%, optical purity: 100% ee).

EXAMPLE 12

According to the same manner as that described in Example 1 except for using a 5 liter four-necked flask, using racemic bromomethyl-3'-chlorophenylcarbinol (10 g), vinyl acetate (93.4 g), methyl-tert-butylether (2500 g), BHT (600 mg) and Lipase QL (50 g, manufactured by Meito Sangyo Co., Ltd.) and stirring at a temperature in a range from 45° to 50° C. for 7 hours, the mixture was subjected to a lipase treatment and then filtered.

The amount of (R)-bromomethyl-3'-chlorophenylcarbinol contained in the filtrate was 3.7 g and the optical purity was 100% ee.

According to the same manner as that described in Example 1 except for concentrating this filtrate to obtain a solution of 240 ml, adding dropwise aqueous 2N sodium hydroxide solution (100 g) over 1.5 hours and extracting the aqueous layer with methyl-tert-butylether (50 ml) in place of hexane after phase separating the oil layer, the filtrate was subjected to a sodium hydroxide treatment, extracted, dried, filtered and then concentrated.

The amount of (R)-3'-chlorostyrene oxide contained in the resulting residue was 2.2 g and the optical purity was 100% ee.

According to the same manner as that described in Example 1, the residue was distilled to obtain 1.5 g of (R)-3'-chlorostyrene oxide (chemical purity: 99.2%, optical purity: 100% ee).

Reference Example 1

To a mixture of tetrahydrofuran (30 ml) and sodium borohydride (8.56 mmol, 0.334 g), dimethyl sulfate (8.56 mmol, 1.102 g) was added at 40° C. under a nitrogen flow, and the mixture was stirred with maintaining at a temperature in a range from 45° to 50° C. for one hour.

Then, a solution of (1S,2R)-norephedrine (0.856 mmol, 0.1294 g) and tetrahydrofuran (2 ml) was added at the same temperature, followed by stirring at the same temperature for 1.5 hours. A solution of 2-bromo-3'-chloroacetophenone (4.28 mmol, 1 g) and tetrahydrofuran (20 ml) was added dropwise over 30 minutes, followed by stirring at the same temperature for 0.5 hours.

After the reaction, the reaction mixture was cooled to 10° C. and a hydrochloric acid/methanol solution (concentrated hydrochloric acid was diluted with methanol to give an aqueous 1N hydrochloric acid) (85 ml). After stirring for one hour, the solvent was distilled off and toluene (200 ml) and 7% hydrochloric acid (50 ml) were added to extract the solution. The organic layer was washed with aqueous sodium bicarbonate, washed with water and dried over anhydrous magnesium sulfate. Then, the solvent was distilled off to obtain 0.91 g of (R)-3'-chlorophenylbromomethylcarbinol. The optical purity was 84.6%.

Reference Examples 2 to 6

According to the same manner as that described in Reference Example I except for using (S)-leucinol (0.856 mmol, 0.1 g), (R)-phenylglycinol (0.856 mmol, 0.117 g), (1S,2R)-2-amino-1,2-diphenylethanol (0.856 mmol, 0.183 g), (S)-valinol (0.856 mmol, 0.088 g) or (R)-5,5-diphenyl-2-methyl-3,4-propano-1,3,2-oxaborolysine (0.856mmol, 0.237 g) in place of (1S,2R)-norephedrine, the reaction and the post treatment were carried out. The results are shown in Table 1.

TABLE 1

| Reference Example No. | Amino alcohol | Optical yield |
|---|---|---|
| 2 | (S)-Leucinol | 72% ee (S) |
| 3 | (R)-Phenylglycinol | 71% ee (R) |
| 4 | (1S,2R)-2-Amino-1,2-diphenylethanol | 91% ee (R) |
| 5 | (S)-Valinol | 90% ee (S) |
| 6 | (R)-5,5-diphenyl-2-methyl-3,4-propano-1,3,2-oxaborolysine | 87% ee (R) |

Reference Example 7

To a mixture of tetrahydrofuran (1 ml) and (1S,2R)-1,2-diphenyl-2-aminoethanol (0.0447 g), a borane-THF (1M) solution (4.4 ml) was added under a nitrogen flow. After heating to 45° C., the mixture was stirred at a temperature in a range from 45° to 50° C. for 1.5 hour. Then, a solution of 2-bromo-3'-chloroacetophenone (1 g) and THF (20 ml) was added at the same temperature over minutes, followed by stirring at the same temperature for 20 minute. After cooling to 10° C., a solution (1M, 0.2 ml) prepared by diluting hydrochloric acid with methanol was added.

Then, the low-boiling fraction was distilled off by concentrating under reduced pressure and, after mixing the residue with toluene (200 ml), a hydrochloride salt of (1S,2R)-1,2-diphenyl-2-aminoethanol was filtered and washed with toluene (100 ml). The resulting filtrate and the wash were combined, and then the mixture was washed with water (20 ml) and dried. The solvent was distilled off to obtain 0.97 g of (R)-3'-chlorophenylcarbinol. The optical purity was 91.2%.

What is claimed is:

1. A process for producing substantially optically pure (R)-styrene oxides represented by the general formula (1):

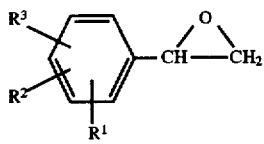 (1)

wherein $R^1$ is a halogen atom, a lower alkyl group, a lower alkoxy group or a trifluoromethyl group; $R^2$ and $R^3$ independently indicate a hydrogen atom, a halogen atom, a lower alkyl group, a lower alkoxy group or a trifluoromethyl group, or $R^2$ and $R^3$ together form a methylenedioxy group;, which comprises treating a mixture of (R)- and (S)-phenylhalogenomethylcarbinols represented by the formula (2):

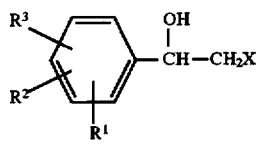 (2)

wherein said mixture of (R)- and (S)-phenylhalogenomethylcarbinols is one enriched with (R)-phenylhaloqenomethylcarbinols, and wherein $R^1$, $R^2$ and $R^3$ are as defined above and X is halogen atom, with a lipase in the presence of a carboxylate to preferentially convert the (S)-phenylhalogenomethylcarbinols (2) into (S)-carbinol alkylates represented by the formula (3):

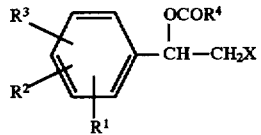 (3)

wherein $R^1$, $R^2$ and $R^3$ and X are as defined above, and $R^4$ is a substituted or non-substituted lower alkyl group, and treating a mixture of the formed carbinol alkylates (3) and (R)-phenylhalogenomethylcarbinols (2) with a base to cyclize the (R)-phenylhalogenomethylcarbinols (2).

2. The process according to claim 1, wherein the lipase treatment is carried out further in the presence of a phenolic compound.

3. The process according to claim 1, wherein the lipase is produced by Alcaligenes species, Achromobacter species and Pseudomonas species.

4. The process according to claim 1, wherein the carboxylate is an ester of a C2–C18 carboxylic acid.

5. The process according to claim 4, wherein the carboxylate is a vinyl ester or isopropenyl ester of a C2–C18 carboxylic acid.

6. The process according to claim 4, wherein the carboxylate is an ester of acetic acid or chloroacetic acid.

7. The process according to claim 2, wherein the phenolic compound is selected from the group consisting of 2,6-di-tert-butyl-4-methylphenol, 2,6-di-tert-butylphenol and 2-tert-butyl-4-methylphenol.

8. The process according to claim 1, wherein the (R)-styrene oxides are selected from the group consisting of (R)-3'-chlorostyrene oxide, (R)-3'-bromostyrene oxide, (R)-3'-fluorostyrene oxide, (R)-3'-methylstyrene oxide, (R)-3'-methoxystyrene oxide and (R)-3'-trifluoromethylstyrene oxide.

9. The process according to claim 1, wherein content of (R)-phenylhalogenomethylcarbinols in the mixture of (R)- and (S)-phenylhalogenomethylcarbinols is at least 70% by weight.

10. The process according to claim 9, wherein the content is at least 80% by weight.

11. The process according to claim 1, wherein said (R)-styrene oxides represented by the general formula (1) have an optical purity of 100% ee.

12. The process according to claim 1, wherein the lipase used in an amount of about 0.1–10% by weight to the (S)-phenylhalogenomethylcarbinols (2).

13. The process according to claim 1, wherein the lipase is used in an amount exceeding 10% by weight to the (S)-phenylhalogenomethylcarbinols (2).

14. The process according to claim 1, wherein the lipase is recovered by filtration.

15. The process according to claim 1, wherein the cyclization of (R)-phenylhalogenomethylcarbinols (2) is conducted with 1 to 3N sodium hydroxide at about 0° to 20° C.

16. The process according to claim 1, wherein the cyclization of (R)-phenylhalogenomethylcarbinols (2) is conducted with potassium carbonate at about 30° to 100° C.

17. A process for producing substantially optically pure (R)-styrene oxides represented by the general formula (1):

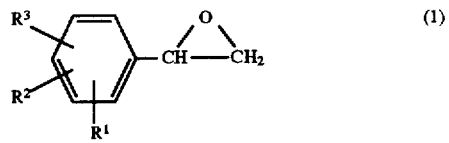 (1)

wherein $R^1$ is a halogen atom, a lower alkyl group, a lower alkoxy group or a trifluoromethyl group; $R^2$ and $R^3$ independently indicate a hydrogen atom, a halogen atom, a lower alkyl group, a lower alkoxy group or a trifluoromethyl group, or $R^2$ and $R^3$ together form a methylenedioxy group;, which comprises treating a mixture of (R)- and (S)-phenylhalogenomethylcarbinols represented by the formula (2):

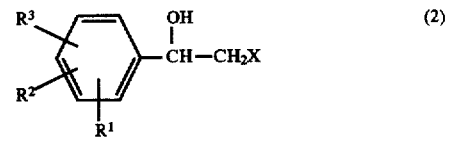 (2)

wherein said mixture of (R)- and (S)-phenylhalogenomethylcarbinols is one enriched with (R)-phenylhaloqenomethylcarbinols, and wherein $R^1$, $R^2$ and $R^3$ are as defined above and X is halogen atom, with a lipase in the presence of a carboxylate to preferentially convert the (S)-phenylhaloqenomethylcarbinols (2) into (S)-carbinol alkylates represented by the formula (3):

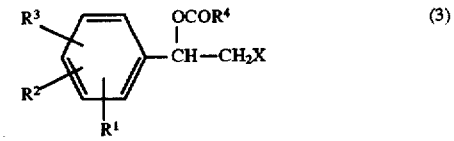 (3)

wherein $R^1$, $R^2$ and $R^3$ and X are as defined above, and $R^4$ is a substituted or non-substituted lower alkyl group, and treating a mixture of the formed carbinol alkylates (3) and (R)-phenylhalogenomethylcarbinols (2) with a base to cyclize the (R)-phenylhalogenomethylcarbinols (2);

wherein the mixture of (R)- and (S)-phenylhalogenomethylcarbinols is obtained by reducing phenyl halogenomethyl ketones represented by the formula (4):

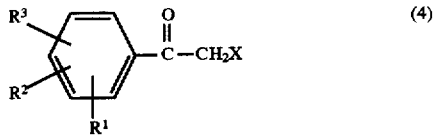
(4)

wherein $R^1$, $R^2$ and $R^3$ and X are as defined above, with an asymmetric reducing agent which is obtained from boranes and a β-amino alcohol, in which an absolute configuration of β-carbon is R, represented by the formula (5):

(5)

wherein $R^5$ is an alkyl group having 1 to 7 carbon atoms, a non-substituted or substituted aryl group, or a non-substituted or substituted aralkyl group; $R^6$ is a hydrogen atom, a lower alkyl group, or an non-substituted or substituted aralkyl group, or $R^5$ and $R^6$ together form a lower alkylene group; $R^7$ and $R^8$ independently indicate a hydrogen atom, an alkyl group having 1 to 7 carbon atoms, or a lower alkylene group; and $R^7$ and $R^8$ together form a non-substituted or substituted aryl group; or $R^7$ and $R^5$ together form a non-substituted or a benzene ring-fused lower alkylene group, or obtained from the β-amino alcohol (5), a metal borohydride and an acid or a dialkyl sulfate.

18. The process according to claim 17, wherein the asymmetric reducing agent is obtained from the β-amino alcohol (5), the metal borohydride and the acid or the dialkyl sulfate.

* * * * *